United States Patent
Yabuguchi et al.

(10) Patent No.: US 10,323,105 B2
(45) Date of Patent: Jun. 18, 2019

(54) WATER-ABSORBENT RESIN AND ABSORBENT ARTICLE

(71) Applicant: Sumitomo Seika Chemicals Co. Ltd., Kako-gun (JP)

(72) Inventors: Hiroki Yabuguchi, Himeji (JP); Tetsuhiro Hinayama, Himeji (JP); Maoki Hama, Himeji (JP); Hideki Yokoyama, Himeji (JP)

(73) Assignee: Sumitomo Seika Chemicals Co. Ltd., Kako-gun (JP)

( * ) Notice: Subject to any disclaimer, the term of this patent is extended or adjusted under 35 U.S.C. 154(b) by 0 days.

(21) Appl. No.: 15/324,764

(22) PCT Filed: Nov. 4, 2014

(86) PCT No.: PCT/JP2014/079243
§ 371 (c)(1),
(2) Date: Jan. 9, 2017

(87) PCT Pub. No.: WO2016/006130
PCT Pub. Date: Jan. 14, 2016

(65) Prior Publication Data
US 2017/0218096 A1    Aug. 3, 2017

(30) Foreign Application Priority Data

Jul. 11, 2014 (JP) ................................ 2014-143715
Oct. 31, 2014 (JP) ................................ 2014-223722

(51) Int. Cl.

| | | |
|---|---|---|
| *C08F 20/06* | (2006.01) | |
| *C08J 3/24* | (2006.01) | |
| *C08F 8/14* | (2006.01) | |
| *A61F 13/49* | (2006.01) | |
| *A61F 13/53* | (2006.01) | |
| *C08F 2/32* | (2006.01) | |
| *A61L 15/60* | (2006.01) | |
| *C08F 8/00* | (2006.01) | |
| *C08F 220/06* | (2006.01) | |
| *A61L 15/24* | (2006.01) | |
| *B01J 20/26* | (2006.01) | |

(52) U.S. Cl.
CPC .............. *C08F 8/14* (2013.01); *A61F 13/49* (2013.01); *A61F 13/53* (2013.01); *A61L 15/24* (2013.01); *A61L 15/60* (2013.01); *B01J 20/267* (2013.01); *C08F 2/32* (2013.01); *C08F 8/00* (2013.01); *C08F 220/06* (2013.01); *C08J 3/24* (2013.01); *C08F 20/06* (2013.01)

(58) Field of Classification Search
CPC .......... C08F 8/14; C08F 20/06; C08F 120/06; C08F 220/06; C08J 3/24; C08J 3/245; A61L 15/24; A61L 15/60; B01J 20/267

See application file for complete search history.

(56) References Cited

U.S. PATENT DOCUMENTS

| | | | |
|---|---|---|---|
| 5,180,798 A | 1/1993 | Nakamura et al. | |
| 5,562,646 A | 10/1996 | Goldman et al. | |
| 5,624,967 A | 4/1997 | Hitomi et al. | |
| 5,760,080 A | 6/1998 | Wada et al. | |
| 6,150,582 A * | 11/2000 | Wada ................ | A61F 13/15203 604/358 |
| 8,846,823 B2 | 9/2014 | Nakamura et al. | |
| 9,669,386 B2 | 6/2017 | Wada et al. | |
| 2008/0032888 A1* | 2/2008 | Nakamura .............. | A61L 15/60 502/402 |
| 2010/0009846 A1 | 1/2010 | Ikeuchi et al. | |
| 2013/0175473 A1* | 7/2013 | Wada ................. | B01J 20/28011 252/194 |
| 2014/0031203 A1 | 1/2014 | Kondo et al. | |
| 2014/0194574 A1 | 7/2014 | Handa et al. | |

FOREIGN PATENT DOCUMENTS

| | | |
|---|---|---|
| CN | 102875944 A | 1/2013 |
| CN | 103153455 A | 6/2013 |
| EP | 1882701 A1 | 1/2008 |

(Continued)

OTHER PUBLICATIONS

Supplementary Search Report dated Mar. 17, 2017, issued for European Patent Application No. 14897322.5.
Notice of Reasons for Rejection dated Dec. 2, 2014, issued to JP Application No. 2014-223722.
International Search Report dated Dec. 2, 2014, issued for PCT/JP2014/079243.
Experimental result report and partial English translation (Kou 2-1) dated Jul. 6, 2016, by T. Matsumoto.
Experimental result report (Kou 2-2) dated Jul. 6, 2016, by T. Matsumoto.
Experimental result report (Kou 4) and partial English translation dated Jul. 4, 2016, by T. Matsumoto.

(Continued)

*Primary Examiner* — Roberto Rabago
(74) *Attorney, Agent, or Firm* — Locke Lord LLP

(57) ABSTRACT

Provided are: a water-absorbent resin which, when used as an absorbent material, retains a high water-absorption performance, increases the diffusivity of a to-be-absorbed liquid and makes it possible to effectively decrease the amount of re-wet; and an absorbent article formed using an absorbent material including the water-absorbent resin. The water-absorbent resin according to the present invention is a water-absorbent resin obtained by polymerizing a water-soluble ethylenically monomer in the presence of an internal-crosslinking agent and thereafter post-crosslinking the polymer with a post-crosslinking agent, characterized in that when subjected to a liquid flow test, the water-absorbent resin has an effective absorbent material index (K) indicated by equation (I) of 250 or greater.

Effective absorbent material index $(K) = $[(the amount of liquid flow) (g)]×[(artificial-urine absorption ratio) (g/g)]   (I)

6 Claims, 2 Drawing Sheets

(56) References Cited

FOREIGN PATENT DOCUMENTS

| | | | |
|---|---|---|---|
| EP | 2116571 A1 | 11/2009 | |
| EP | 2623198 A1 | 8/2013 | |
| EP | 2700659 A1 | 2/2014 | |
| EP | 2893974 A1 | 7/2015 | |
| JP | 03-227301 A | 10/1991 | |
| JP | 05-078420 A | 3/1993 | |
| JP | 06-287233 A | 10/1994 | |
| JP | 06-345819 A | 12/1994 | |
| JP | 08-057310 A | 3/1996 | |
| JP | 08-057311 A | 3/1996 | |
| JP | 08-120013 A | 5/1996 | |
| JP | 08-188602 A | 7/1996 | |
| JP | 09-124710 A | 5/1997 | |
| JP | 09-194514 A | 7/1997 | |
| JP | 09-510889 A | 11/1997 | |
| JP | 11-029605 A | 2/1999 | |
| JP | 11-058615 A | 3/1999 | |
| JP | 11-335404 A | 12/1999 | |
| JP | 2002-179712 A | 6/2002 | |
| JP | 2003-088551 A | 3/2003 | |
| JP | 2005-344103 | * | 12/2005 |
| JP | 2005-344103 A | 12/2005 | |
| JP | 2008-280459 A | 11/2008 | |
| JP | 2009-019065 A | 1/2009 | |
| JP | 2009-509723 A | 3/2009 | |
| JP | 2009-280668 A | 12/2009 | |
| JP | 2012041439 A | 3/2012 | |
| JP | 2012-236898 A | 12/2012 | |
| WO | 2005097313 A1 | 10/2005 | |
| WO | 2005/108472 A1 | 11/2005 | |
| WO | 2007/037453 A1 | 4/2007 | |
| WO | 2008/096713 A1 | 8/2008 | |
| WO | 2009150984 A1 | 12/2009 | |
| WO | 2012/043821 A1 | 4/2012 | |
| WO | WO 2012/043821 | * | 4/2012 |
| WO | 2012/144564 A1 | 10/2012 | |
| WO | 2014/038324 A1 | 3/2014 | |

OTHER PUBLICATIONS

Experimental result report (Kou 7) dated Jul. 27, 2016, by T. Matsumoto.
Written Opposition dated Oct. 19, 2016, issued for Japanese Patent No. 5893117.
Office Action dated Mar. 19, 2018 issued for corresponding European Patent Application No. 14897322.5.
Office Action dated on Jul. 30, 2018 issued for corresponding Chinese Patent Application No. 2014 800 80354.X.
Office Action dated Dec. 5, 2018, issued in the EP Patent Application No. 14897322.5.

* cited by examiner

WATER-ABSORBENT RESIN AND ABSORBENT ARTICLE

TECHNICAL FIELD

The present invention relates to a water-absorbent resin and an absorbent article, and more specifically relates to a water-absorbent resin forming an absorbent material suitably used for hygienic materials such as disposable diapers, sanitary napkins and incontinence pads as well as an absorbent article comprising the water-absorbent resin.

BACKGROUND ART

In recent years, water-absorbent resins have been widely used in the field of hygienic materials such as disposable diapers, sanitary napkins and incontinence pads.

For water-absorbent resins as described above, cross-linked products of partially neutralized polymers of acrylic acid salt are preferred because they have many advantages, including the followings: they have better water absorption performance; their raw materials such as acrylic acid has easy industrial availability, and therefore they can be produced with stable quality and low cost; and they are more resistant to decomposition and deterioration.

An absorbent article such as a disposable diaper, a sanitary napkin and an incontinence pad comprises an absorbent material usually arranged at the central part thereof to absorb and hold a body fluid excreted from the body such as urine and menstrual blood, a liquid-permeable front sheet (a top sheet) arranged on a side to make contact with the body, and a liquid-impermeable back sheet (a back sheet) arranged opposite to the side to make contact with the body. Further, the absorbent material comprises a hydrophilic fiber such as pulp and a water-absorbent resin.

In recent years, there have been increasing demands for thinner and lighter absorbent articles in view of excellent designability, convenient portability, efficient distributability and the like. Further, there have been increasing needs for so-called eco-friendly production where resource are effectively utilized to minimizing the usage of slowly growing natural materials such as trees in view of environmental conservation. Methods of producing a thinner absorbent article which are conventionally performed include, for example, a method in which the amount of a hydrophilic fiber such as crushed wood pulp, which serves to fix a water-absorbent resin in an absorbent material, is reduced while the amount of a water-absorbent resin is increased.

An absorbent material having a low ratio of a hydrophilic fiber and a large amount of water-absorbent resin is preferred for thinner in view of a reduced bulky hydrophilic fiber and a liquid holding capacity. However, in the case that a load due to deformation, pressure and the like may be applied to an absorbent material comprising a water-absorbent resin, for example, when an infant wearing a thinner absorbent article sits down, the re-wet of a to-be-absorbed liquid (the return of a liquid) may not be able to be fully prevented. Further, such an absorbent article cannot accommodate multiple urinations, resulting in giving discomfort to a wearer.

Moreover, a large amount of a water-absorbent resin becomes a soft gel-like material when it absorbs a liquid, and a load further applied to this gel may cause the so-called "gel blocking phenomenon", resulting in significantly reduced liquid diffusibility, which in turn may slow the speed of permeation of a liquid for an absorbent material. This "gel blocking phenomenon" is explained below. When an absorbent material containing particularly highly densified water-absorbent resins absorbs liquid, a water-absorbent resin near the surface layer absorbs the liquid to further densify a soft gel around the surface layer, and so liquid permeation into the absorbent material is inhibited, preventing the internal water-absorbent resins from efficiently absorbing the liquid.

Accordingly, the followings have been so far proposed as means for preventing problems which may occur when a hydrophilic fiber is reduced and a large amount of a water-absorbent resin is used: for example, a method in which a hydrogel absorptive polymer is used having a specific saline-flow inductivity, under-pressure performance and the like (see Patent Document 1); a method in which a water-absorbent resin is used obtained from heat treatment of a specific water-absorbent resin precursor with a specific surface crosslinking agent (see Patent Document 2); and the like.

However, these methods cannot necessarily satisfy an absorption performance expected for an absorbent material having a large amount of a water-absorbent resin. Further, they tend to cause a problem in that, for example, a to-be-absorbed liquid may not be captured, resulting in liquid leakage.

PRIOR ART DOCUMENT

Patent Documents

Patent Document 1: Japanese Unexamined Patent Application (Translation of PCT Application), Publication No. H09-510889

Patent Document 2: Japanese Unexamined Patent Application, Publication No. H08-57311

DISCLOSURE OF THE INVENTION

Problems to be Solved by the Invention

The present invention is made in view of aforementioned circumstances. An objective of the present invention is to provide a water-absorbent resin allowing for a high diffusibility of a to-be-absorbed liquid to reduce the amount of re-wet while maintaining a high water absorption capacity when used for an absorbent material. Another objective is to provide an absorbent article using an absorbent material comprising the aforementioned water-absorbent resin.

Means for Solving the Problems

The present inventors have conducted extensive studies in order to solve the above problems. As a result, the present inventors have found that a better absorption performance can be obtained in evaluation of an absorbent article when a water-absorbent resin showing an absorbent material effective index K of a specific value or more is used. The absorbent material effective index K is calculated by multiplying the artificial-urine absorption ratio (g/g) by the amount of liquid flow (g) obtained from a specific liquid flow test. That is, the present invention provides the followings.

(1) The present invention provides a water-absorbent resin obtained by polymerizing a water-soluble ethylenically unsaturated monomer in the presence of an internal-cross-linking agent, and performing post-crosslinking with a post-crosslinking agent, wherein the water-absorbent resin shows an absorbent material effective index K of 250 or more as determined in a liquid flow test defined below using the water-absorbent resin, the absorbent material effective index K being defined by the formula (I):

$$\text{Absorbent material effective index } K = \text{the amount of liquid flow (g)} \times \text{the artificial-urine absorption ratio (g/g)} \quad (I)$$

[Liquid Flow Test]

the liquid flow test being performed as follows: a nonwoven is placed on an acrylic plate, and 4.8 g of the water-absorbent resin is uniformly dispersed thereon, and then another nonwoven is placed thereover so as to form a sandwiched configuration to give a measurement sample. Next, an acrylic plate having a cylinder-like inlet part with an inner diameter of 3 cm at the center is placed thereover so that the center of the cylinder coincides with the center of the measurement sample, and then 120 g of artificial-urine at a liquid temperature of 25° C. is introduced in one portion through the cylinder-like inlet part, and the amount of artificial-urine flowed out of the acrylic plate is measured, thereby obtaining the amount of liquid flow (g).

(2) Further, the present invention provides the water-absorbent resin according to (1), wherein the artificial-urine absorption ratio is 30.0 g/g or more.

(3) Further, the present invention provides the water-absorbent resin according to (1) or (2), wherein the amount of liquid flow is 5.0 g or more.

(4) The present invention provides an absorbent article using an absorbent material comprising the water-absorbent resin according to any one of (1) to (3).

Effects of the Invention

The present invention can provide a water-absorbent resin allowing for a high diffusibility of a to-be-absorbed liquid to reduce the amount of re-wet while maintaining a high water absorption capacity when used for an absorbent material. The present invention also can provide an absorbent article using an absorbent material comprising the aforementioned water-absorbent resin.

PREFERRED MODE FOR CARRYING OUT THE INVENTION

Figure 1:
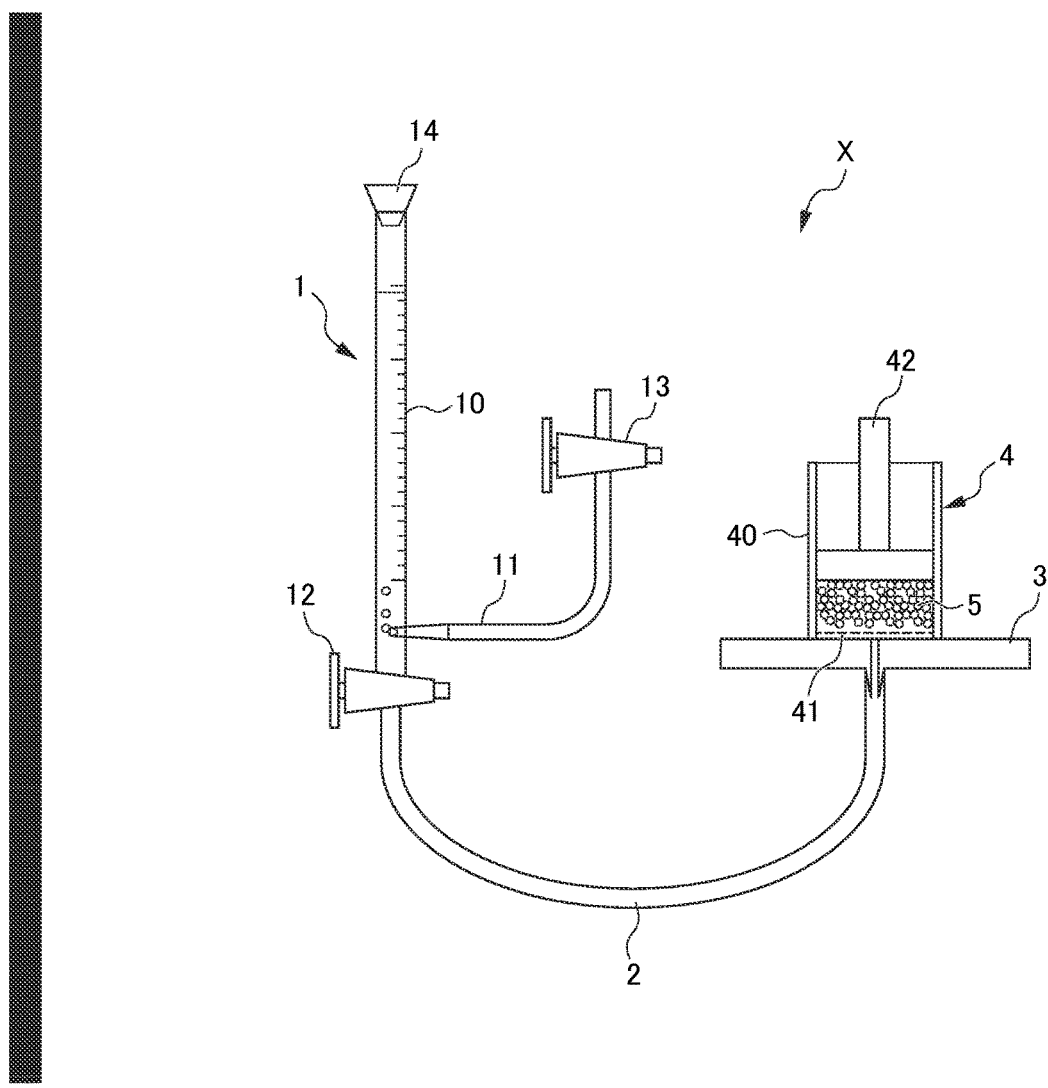
FIG. 1 shows a pattern diagram illustrating the schematic arrangement of an apparatus for measuring, in a water-absorbent resin, a water absorption capacity of physiological saline under a load of 4.14 kPa.

The present invention will be described in detail below.

1. Water-Absorbent Resin

The water-absorbent resin according to the present invention has those properties described below.

The water-absorbent resin according to the present invention is characterized by that it is a water-absorbent resin obtained by polymerizing a water-soluble ethylenically unsaturated monomer in the presence of an internal-crosslinking agent, and performing post-crosslinking with a post-crosslinking agent, wherein the absorbent material effective index K defined by the formula (I) is 250 or more.

$$\text{Absorbent material effective index } K = \text{the amount of liquid flow (g)} \times \text{the artificial-urine absorption ratio (g/g)} \quad (I)$$

[Liquid Flow Test]

Liquid flow tests are performed as follows: a nonwoven is placed on an acrylic plate, and 4.8 g of a water-absorbent resin is uniformly dispersed thereon, and then another nonwoven is placed thereover so as to form a sandwiched configuration. This is taken as a measurement sample. An acrylic plate having a cylinder-like inlet part with an inner diameter of 3 cm at the center is placed thereover so that the center of the cylinder coincides with the center of the measurement sample. Then, 120 g of artificial-urine at a liquid temperature of 25° C. is introduced in one portion through the cylinder-like inlet part, and the amount of artificial-urine flowed out of the acrylic plate is measured to obtain the amount of liquid flow (g).

Note that the absorbent material effective index K of a water-absorbent resin is preferably 300 or more, more preferably 350 or more, and further preferably 400 or more. Further, the upper limit of the absorbent material effective index K is preferably 1000 or less.

The water-absorbent resin according to the present invention preferably has an artificial-urine absorption ratio of 30.0 g/g or more. The artificial-urine absorption ratio refers to a mass of artificial-urine which a water-absorbent resin per unit mass can absorb, and represents the degree of a liquid absorption capacity of the water-absorbent resin. Note that the artificial-urine absorption ratio is more preferably 32.0 g/g or more, further preferably 34.0 g/g or more, and further more preferably 36.0 g/g or more. Further, the upper limit of the artificial-urine absorption ratio is preferably 60.0 g/g or less.

Further, the water-absorbent resin according to the present invention preferably has an amount of liquid flow of 5.0 g or more as measured by the "liquid flow test" described above. The amount of liquid flow serves as a measure of the diffusibility of a liquid introduced into an absorbent material as described above. Note that the amount of liquid flow is more preferably 6.0 g or more, further preferably 8.0 g or more, and further more preferably 10.0 g or more. Further, the upper limit of the amount of liquid flow is preferably 50.0 g/g or less.

Further, in the water-absorbent resin according to the present invention, the water-absorption capacity of physiological saline under a load of 4.14 kPa at 60 minutes from the start of water absorption is preferably 16 ml/g or more. In general, in the case of a water-absorbent resin which slowly absorbs a liquid over a long period of time, the amount of re-wet tends to be large, for example, when a pressure is applied to an absorbent material comprising that water-absorbent resin (for example, when an infant wearing a diaper comprising that absorbent material sits down immediately after urination). For example, in a case where a water-absorbent resin having a higher water-absorption capacity of physiological saline under a load of 4.14 kPa is used for a hygienic material, the amount of re-wet is smaller when pressure is applied to the hygienic material.

Note that the water-absorption capacity of physiological saline under a load of 4.14 kPa at 60 minutes from the start of water absorption is preferably 16 ml/g or more, more preferably 20 ml/g or more, and further preferably 24 ml/g or more. Further, the water-absorption capacity of physiological saline under a load of 4.14 kPa at 60 minutes from the start of water absorption is preferably 50 ml/g or less, more preferably 40 ml/g or less.

Further, the water-absorbent resin according to the present invention preferably has a median particle diameter of 200 to 600 μm, more preferably 250 to 500 μm, further preferably 300 to 450 μm and further more preferably 350 to 450 μm.

Further, in the water-absorbent resin according to the present invention, the mass proportion of particles from 150 to 850 μm relative to the whole proportion is preferably 85 mass % or more, more preferably 90 mass % or more, and further preferably 95 mass % or more. Further, the mass proportion of particles from 300 to 400 μm relative to the whole proportion is preferably 20 mass % or more, and more preferably 25 mass % or more.

Note that particles of water-absorbent resin may be in a form where each comprises a single particle, or may be in a form where fine particles (primary particles) are agglomerated (secondary particles). Forms of the primary particles include a substantially spherical form, an irregular fractured form, a plate-like form and the like. In a case of primary particles produced by reversed phase suspension polymerization, their forms include a substantially spherical single particle form having a smooth surface profile such as a true spherical shape and an elliptically spherical shape. Then, the flowability as powder is high because primary particles in such forms have a smooth surface. Further, agglomerated particles are not easily destroyed upon impact, and thus a water-absorbent resin having high particle strength can be formed because agglomerated particles tend to be more densely packed.

The amount of liquid flow, the artificial-urine absorption ratio, the water-absorption capacity of physiological saline under a load of 4.14 kPa and the median particle diameter of the aforementioned water-absorbent resin can all be evaluated by the evaluation test methods described in Examples below.

Note that an additive may be blended depending on the purposes in order to provide various preferred properties on the resulting water-absorbent resin. Such additives include inorganic powders, surfactants, oxidizing agents, reducing agents, metal chelating agents, radical chain inhibitors, antioxidizing agents, antibacterial agents, deodorizing agents and the like. For example, the fluidity of a water-absorbent resin can be improved by adding 0.05 to 5 parts by mass of amorphous silica as an inorganic powder relative to 100 parts by mass of the water-absorbent resin.

2. Method of Producing Water-Absorbent Resin

The water-absorbent resin according to the present invention can be produced by polymerizing a water-soluble ethylenically unsaturated monomer in the presence of an internal-crosslinking agent.

The methods of polymerizing a water-soluble ethylenically unsaturated monomer include typical polymerization methods such as the aqueous polymerization method, the emulsion polymerization method, the reversed phase suspension polymerization method. In the aqueous polymerization method, polymerization is performed by heating an aqueous solution of a water-soluble ethylenically unsaturated monomer, if desired, with stirring. Further, in the reversed phase suspension polymerization method, polymerization is performed by heating a water-soluble ethylenically unsaturated monomer in a hydrocarbon dispersion medium with stirring. In the present invention, the reversed phase suspension polymerization method is preferred because precise control of a polymerization reaction and extensive control of particle diameters are possible.

An example of the methods of producing the water-absorbent resin according to the present invention will be described below.

Specific examples of the method of producing a water-absorbent resin include a method of producing a water-absorbent resin by performing reversed phase suspension polymerization of a water-soluble ethylenically unsaturated monomer in a hydrocarbon dispersion medium, the method comprising the steps of: performing polymerization step in the presence of an internal-crosslinking agent and in the presence of at least an azo based compound and a peroxide; and performing post-crosslinking step of a hydrous gel-like material having an internal-crosslinking structure obtained from the polymerization in the presence of a post-crosslinking agent.

<Polymerization Step>
[Water-Soluble Ethylenically Unsaturated Monomer]

Water-soluble ethylenically unsaturated monomers include, for example, (meth)acrylic acid ("(meth)acry" herein refers to both "acry" and "methacry". The same shall apply hereinafter) and salts thereof; 2-(meth)acrylamide-2-methylpropanesulfonic acid and salts thereof; nonionic monomers such as (meth)acrylamide, N,N-dimethyl(meth)acrylamide, 2-hydroxyethyl(meth)acrylate, N-methylol (meth)acrylamide, polyethylene glycol mono(meth)acrylate; amino group-containing unsaturated monomers such as N,N-diethylaminoethyl(meth)acrylate, N,N-diethylaminopropyl(meth)acrylate, diethylaminopropyl(meth)acrylamide and quaternary compounds thereof. Among these water-soluble ethylenically unsaturated monomers, (meth)acrylic acid or salts thereof, (meth)acrylamide, N,N-dimethylacrylamide are preferred in view of easy industrial availability, and (meth)acrylic acid and salts thereof are more preferred. Note that these water-soluble ethylenically unsaturated monomers may be used alone or in combination of two or more.

Among these, acrylic acid and salts thereof are widely used as raw materials for water-absorbent resins, and those materials may be used in which the aforementioned other water-soluble ethylenically unsaturated monomers are copolymerized with these partially neutralized acrylates. In this case, a partially neutralized acrylate is preferably used as a main water-soluble ethylenically unsaturated monomer in an amount of 70 to 100 mol % relative to the total amount of water-soluble ethylenically unsaturated monomers.

A water-soluble ethylenically unsaturated monomer is preferably dispersed in a hydrocarbon dispersion medium in the state of an aqueous solution, and subjected to reversed phase suspension polymerization. A water-soluble ethylenically unsaturated monomer in the form of an aqueous solution can increase the dispersion efficiency in a hydrocarbon dispersion medium. The concentration of a water-soluble ethylenically unsaturated monomer in the aqueous solution is preferably in a range from 20 mass % to the saturation concentration. Further, the concentration of a water-soluble ethylenically unsaturated monomer is more preferably 55 mass % or less, further preferably 50 mass % or less and further more preferably 45 mass % or less. On the other hand, the concentration of a water-soluble ethylenically unsaturated monomer is more preferably 25 mass % or more, further preferably 28 mass % or more, and further more preferably 30 mass % or more.

When a water-soluble ethylenically unsaturated monomer has an acid group such as (meth)acrylic acid, 2-(meth)acrylamide-2-methylpropanesulfonic acid, those having the acid group pre-neutralized with an alkaline neutralizer may be used, if desired. Such alkaline neutralizers include alkali metal salts such as sodium hydroxide, sodium carbonate, sodium hydrogen carbonate, potassium hydroxide, potassium carbonate; ammonia and the like. Further, these alkaline neutralizers may be used in a form of an aqueous solution in order to simply neutralization procedures. Note that the aforementioned alkaline neutralizers may be used alone or in combination of two or more.

For the degree of neutralization of a water-soluble ethylenically unsaturated monomer with an alkaline neutralizer, the degree of neutralization of all acid groups in the water-soluble ethylenically unsaturated monomer is preferably 10 to 100 mol %, more preferably 30 to 90 mol %, further preferably 40 to 85 mol % and further more preferably 50 to 80 mol %.

[Internal-Crosslinking Agent]

The internal-crosslinking agents include those capable of crosslinking a polymer of water-soluble ethylenically unsaturated monomers, including, for example, unsaturated polyesters obtained by allowing polyols, for example, diols and triols such as (poly)ethylene glycol ("(poly)" means that the prefix "poly" is optional. The same shall apply hereinafter), (poly)propylene glycol, 1,4-butanediol, trimethylolpropane, (poly)glycerin to react with unsaturated acids such as (meth)acrylic acid, maleic acid, fumaric acid; bisacrylamides such as N,N-methylenebisacrylamide; di(meth) acrylic acid esters or tri(meth)acrylic acid esters obtained by allowing polyepoxide to react with (meth)acrylic acid; di(meth)acrylic acid carbamyl esters obtained by allowing polyisocyanate such as tolylene diisocyanate, hexamethylene diisocyanate to react with (meth)acrylic acid hydroxyethyl; compounds having two or more polymerizable unsaturated groups, for example, allylated starch, allylated cellulose, diallyl phthalate, N,N',N"-triallylisocyanate, divinylbenzene and the like; polyglycidyl compounds, for example, diglycidyl compounds such as (poly)ethylene glycol diglycidyl ether, (poly)propylene glycol diglycidyl ether, (poly)glycerin diglycidyl ether, triglycidyl compounds and the like; epihalohydrin compounds such as epichlorohydrin, epibromhydrin, α-methyl epichlorohydrin; compounds having two or more reactive functional groups, for example, isocyanate compounds such as 2,4-tolylene diisocyanate, hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol. Among these internal-crosslinking agents, polyglycidyl compounds are preferably used, and glycidyl ether compounds are more preferably used, and (poly)ethylene glycol diglycidyl ether, (poly)propylene glycol diglycidyl ether, (poly)glycerin diglycidyl ether are further preferably used. These internal-crosslinking agents may be used alone or in combination of two or more.

The used amount of the internal-crosslinking agent is preferably 0.000001 to 0.02 mol relative to 1 mol of a water-soluble ethylenically unsaturated monomer, more preferably 0.00001 to 0.01 mol, further preferably 0.00001 to 0.005 mol and further more preferably 0.00005 to 0.002 mol.

[Hydrocarbon Dispersion Media]

Hydrocarbon dispersion media include, for example, aliphatic hydrocarbons having 6 to 8 carbon atoms such as n-hexane, n-heptane, 2-methylhexane, 3-methylhexane, 2,3-dimethylpentane, 3-ethylpentane, n-octane; alicyclic hydrocarbons such as cyclohexane, methylcyclohexane, cyclopentane, methylcyclopentane, trans-1,2-dimethylcyclopentane, cis-1,3-dimethylcyclopentane, trans-1,3-dimethylcyclopentane; aromatic hydrocarbons such as benzene, toluene, xylene and the like. Among these hydrocarbon dispersion media, in particular, n-hexane, n-heptane, cyclohexane are suitably used in view of easy industrial availability, stable quality and low cost. These hydrocarbon dispersion media may be used alone or in combination of two or more. Note that examples of a mixture of hydrocarbon dispersion media include commercially available products such as EXXSOL heptane (made by ExxonMobil Corporation: 75 to 85 mass % of heptane and its isomeric hydrocarbons thereof are contained), which can also produce a suitable result.

The used amount of the hydrocarbon dispersion medium is preferably 100 to 1500 parts by mass relative to 100 parts by mass of a first-step water-soluble ethylenically unsaturated monomer, and more preferably 200 to 1400 parts by mass form the viewpoint that the water-soluble ethylenically unsaturated monomer can be uniformly dispersed to allow for easy control over a polymerization temperature. Note that as described below, reversed phase suspension polymerization is performed in one step (single step) or in multiple steps such as two or more steps, and the first-step polymerization described above means a polymerization reaction of the first step in single-step polymerization or multiple-step polymerization (The same shall apply hereinafter).

[Dispersion Stabilizer]

(Surfactant)

A dispersion stabilizer may be used in reversed phase suspension polymerization in order to improve the dispersion stability of a water-soluble ethylenically unsaturated monomer in a hydrocarbon dispersion medium. A surfactant can be used as the dispersion stabilizer.

As surfactants, the followings may be used: for example, sucrose fatty acid ester, polyglycerin fatty acid, sorbitan fatty acid ester, polyoxyethylene sorbitan fatty acid ester, polyoxyethylene glycerine fatty acid ester, sorbitol fatty acid ester, polyoxyethylene sorbitol fatty acid ester, polyoxyethylene alkyl ether, polyoxyethylene alkyl phenyl ether, polyoxyethylene castor oil, polyoxyethylene hydrogenated castor oil, alkyl allyl formaldehyde condensed polyoxyethylene ether, polyoxyethylene polyoxypropylene block copolymer, polyoxyethylene polyoxy propyl alkyl ether, polyethylene glycol fatty acid ester, alkyl glucoside, N-alkyl gluconamide, polyoxyethylene fatty acid amide, polyoxyethylene alkylamine, phosphate ester of polyoxyethylene alkyl ether, phosphate ester of polyoxyethylene alkyl aryl ether and the like. Among these surfactants, in particular, sorbitan fatty acid ester, polyglycerin fatty acid ester, and sucrose fatty acid ester are preferably used in view of dispersion stability of monomers. These surfactants may be used alone or in combination of two or more.

The used amount of the surfactant is preferably 0.1 to 30 parts by mass relative to 100 parts by mass of a first-step water-soluble ethylenically unsaturated monomer, and more preferably 0.3 to 20 parts by mass.

(Polymeric Dispersion Agent)

Further, a polymeric dispersion agent may also be used, along with a surfactant described above, as a dispersion stabilizer used in reversed phase suspension polymerization.

Polymeric dispersion agents include, for example, maleic anhydride modified polyethylene, maleic anhydride modified polypropylene, maleic anhydride modified ethylene-propylene copolymer, maleic anhydride modified EPDM (ethylene-propylene-diene-terpolymer), maleic anhydride modified polybutadiene, maleic anhydride-ethylene copolymer, maleic anhydride-propylene copolymer, maleic anhydride-ethylene-propylene copolymer, maleic anhydride-butadiene copolymer, polyethylene, polypropylene, ethylene-propylene copolymer, oxidized polyethylene, oxidized polypropylene, oxidized ethylene-propylene copolymer, ethylene-acrylate copolymer, ethyl cellulose, ethyl hydroxyethyl cellulose and the like. Among these polymeric dispersion agents, particularly in view of dispersion stability of monomers, maleic anhydride modified polyethylene, maleic anhydride modified polypropylene, maleic anhydride modified ethylene-propylene copolymer, maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, oxidized ethylene-propylene copolymer are preferably used. These polymeric dispersion agents may be used alone or in combination of two or more.

The used amount of the polymeric dispersion agent is preferably 0.1 to 30 parts by mass relative to 100 parts by mass of a first-step water-soluble ethylenically unsaturated monomer, and more preferably 0.3 to 20 parts by mass.

[Azo Based Compound and Peroxide]

In the above polymerization process, the phrase "in the presence of an azo based compound and a peroxide" does not necessarily means that the azo based compound and the peroxide are coexistent at the beginning of a polymerization reaction, but means that one compound is present before a monomer conversion ratio by radical cleavage due to the other compound becomes 10% or more. However, the both are preferably present in an aqueous solution containing a monomer before the start of the polymerization reaction. Further, an azo based compound and a peroxide may be added to a polymerization reaction system via different flow channels or may be sequentially added to the polymerization reaction system via the same flow channel. Note that an azo based compound and a peroxide to be used may be in the form of powder or an aqueous solution.

(Azo Based Compound)

Azo based compounds include, for example, those azo based compounds such as 1-{(1-cyano-1-methylethyl)azo}formamide, 2,2'-azobis[2-(N-phenyl amidino)propane]dihydrochloride, 2,2'-azobis{2-[N-(4-chlorophenyl)amidino]propane}dihydrochloride, 2,2'-azobis{2-[N-(4-hydroxyphenyl)amidino]propane}dihydrochloride, 2,2'-azobis[2-(N-benzyl amidino)propane]dihydrochloride, 2,2'-azobis[2-(N-allyl amidino)propane]dihydrochloride, 2,2'-azobis(2-amidinopropane)dihydrochloride, 2,2'-azobis{2-[N-(2-hydroxyethyl)amidino]propane}dihydrochloride, 2,2'-azobis[2-(5-methyl-2-imidazoline-2-yl)propane]dihydrochloride, 2,2'-azobis[2-(2-imidazoline-2-yl)propane]dihydrochloride, 2,2'-azobis[2-(4,5,6,7-tetrahydro-1H-1,3-diazepine-2-yl)propane]dihydrochloride, 2,2'-azobis[2-(5-hydroxy-3,4,5,6-tetrahydro-pyrimidine-2-yl)propane]dihydrochloride, 2,2'-azobis{2-[1-(2-hydroxyethyl)-2-imidazoline-2-yl]propane}dihydrochloride, 2,2'-azobis[2-(2-imidazoline-2-yl)propane], 2,2'-azobis{2-methyl-N-[1,1-bis(hydroxymethyl)-2-hydroxyethyl]propionamide}, 2,2'-azobis{2-methyl-N-[1,1-bis(hydroxymethyl)ethyl]propionamide}, 2,2'-azobis[2-methyl-N-(2-hydroxyethyl)propionamide], 2,2'-azobis(2-methylpropionamide)dihydrochloride, 4,4'-azobis-4-cyanovaleinic acid, 2,2'-azobis[2-(hydroxymethyl)propionitrile], 2,2'-azobis[2-(2-imidazoline-2-yl)propane]disulfate dihydrate, 2,2'-azobis[N-(2-carboxyethyl)-2-methylpropione amidine]tetrahydrate, 2,2'-azobis[2-methyl-N-(2-hydroxyethyl)propionamide]. Among these, 2,2'-azobis(2-amidinopropane)dihydrochloride, 2,2'-azobis{2-[1-(2-hydroxyethyl)-2-imidazoline-2-yl]propane}dihydrochloride, 2,2'-azobis[N-(2-carboxyethyl)-2-methylpropione amidine]tetrahydrate are preferred. These azo based compounds may be used alone or in combination of two or more.

(Peroxide)

Peroxides include, for example, persulfates such as potassium persulfate, ammonium persulfate, sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxy isobutyrate, t-butyl peroxy pivalate, hydrogen peroxide. Among these peroxides, potassium persulfate, ammonium persulfate, sodium persulfate, hydrogen peroxide are preferably used, and further, potassium persulfate, ammonium persulfate, sodium persulfate are more preferably used. These peroxides may be used alone or in combination of two or more.

(Used Amount and Used Proportion of Azo Based Compound and Peroxide)

The used amount of an azo based compound and a peroxide is preferably 0.00005 mol or more relative to 1 mol of a water soluble ethylenically unsaturated monomer, more preferably 0.0001 mol or more. Further, the used amount is preferably 0.005 mol or less relative to 1 mol of a water-soluble ethylenically unsaturated monomer, and more preferably 0.001 mol or less.

For the used proportion of an azo based compound and a peroxide, the proportion of the azo based compound is preferably 40 mass % or more relative to the total used amount of the azo based compound and the peroxide, more preferably 50 mass % or more, further preferably 60 mass % or more and further more preferably 70 mass %. On the other hand, the proportion of an azo based compound is preferably 95 mass % or less relative to the total used amount of the azo based compound and the peroxide, more preferably 90 mass % or less, further preferably 85 mass % and further more preferably 80 mass % or less. Further, the range of the mass ratio (azo based compound:peroxide) is preferably 8:12 to 19:1.

[Other Components]

In the method of producing a water-absorbent resin, other components may be added to an aqueous solution containing a water-soluble ethylenically unsaturated monomer to perform reversed phase suspension polymerization, if desired. As other components, various additives such as thickeners, chain transfer agents and the like may be added.

(Thickener)

As an example, a thickener may be added to an aqueous solution containing a water-soluble ethylenically unsaturated monomer to perform reversed phase suspension polymerization. By adding a thickener to adjust the viscosity of an aqueous solution as described above, the median particle diameter resulted from reversed phase suspension polymerization may be controlled.

As a thickener, for example, hydroxyethyl cellulose, hydroxypropyl cellulose, methyl cellulose, carboxymethyl cellulose, polyacrylic acid, (partially) neutralized polyacrylic acid, polyethylene glycol, polyacrylamide, polyethyleneimine, dextrin, sodium alginate, polyvinyl alcohol, polyvinyl pyrrolidone, polyethylene oxide and the like can be used. Note that the following tends to be observed: in a case where the stirring speeds at the time of polymerization are the same, the higher is the viscosity of an aqueous solution of a water-soluble ethylenically unsaturated monomer, the larger is the median particle diameter of the resulting particles.

[Reversed Phase Suspension Polymerization]

When performing reversed phase suspension polymerization, an aqueous monomer solution containing a water-soluble ethylenically unsaturated monomer is dispersed in a hydrocarbon dispersion medium, for example, in the presence of a dispersion stabilizer. When doing this, a dispersion stabilizer (a surfactant and/or a polymeric dispersion agent) may be added either before or after adding the aqueous monomer solution as long as they are added before the start a of polymerization reaction.

In particular, in a view of easy reduction of the amount of a residual hydrocarbon dispersion medium in the resulting water-absorbent resin, it is preferred that polymerization is performed after an aqueous monomer solution is dispersed in a hydrocarbon dispersion medium in which a polymeric dispersion agent has been dispersed, and then a surfactant is further dispersed.

Such a reversed phase suspension polymerization can be performed in a single step or multiple steps such as two or more steps. Further, in view of increasing productivity, it is preferably performed in 2 to 3 steps.

In a case where reversed phase suspension polymerization is performed in multiple steps such as two or more steps, after the first-step reversed phase suspension polymerization is performed, a water-soluble ethylenically unsaturated monomer may be added to the reaction mixture obtained in the first-step polymerization reaction, and mixed to perform a second-step reversed phase suspension polymerization as in the first step. In a case of reversed phase suspension polymerization at each step of the second step and later steps, reversed phase suspension polymerization is preferably performed by adding, in addition to a water-soluble ethylenically unsaturated monomer, an internal-crosslinking agent, an azo compound and a peroxide described above within the aforementioned range of the molar ratio of each component relative to the water-soluble ethylenically unsaturated monomer on the basis of the amount of the water-soluble ethylenically unsaturated monomer to be added in the reversed phase suspension polymerization in each step of the second step and later steps. Note that polymerization is also preferably performed in the presence of an azo based compound and a peroxide in polymerization of the second step and later steps.

The reaction temperature for a polymerization reaction is preferably 20 to 110° C., more preferably 40 to 90° C. from the viewpoint that economy may be improved by allowing rapid progress of a polymerization to reduce a polymerization time, and polymerization heat may be easily removed to perform a smooth reaction. Further, the reaction time is preferably 0.5 to 4 hours.

<Post-Crosslinking Step>

Next, the water-absorbent resin according to the present invention can be obtained by performing post-crosslinking of a hydrous gel-like material having an internal-crosslinking structure obtained by polymerizing a water soluble ethylenically unsaturated monomer using a post-crosslinking agent (post-crosslinking reaction). This post-crosslinking reaction is preferably performed in the presence of a post-crosslinking agent after the polymerization of a water soluble ethylenically unsaturated monomer. By performing a post-crosslinking reaction of a hydrous gel-like material having an internal-crosslinking structure after the polymerization to increase a crosslinking density near a surface of a water-absorbent resin as described above, a water-absorbent resin can be obtained which has various enhanced properties such as a water-absorption capacity under a load and a water-absorption rate.

Post-crosslinking agents can include those compounds having two or more reactive functional groups. They include, for example, polyols such as ethylene glycol, propylene glycol, 1,4-butanediol, trimethylolpropane, glycerin, polyoxyethylene glycol, polyoxypropylene glycol, polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, (poly)glycerol polyglycidyl ether; haloepoxy compounds such as epichlorohydrin, epibromhydrin, α-methyl epichlorohydrin; isocyanate compounds such as 2,4-tolylene diisocyanate, hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol; oxazoline compounds such as 1,2-ethylenebisoxazoline; carbonate compounds such as ethylene carbonate; hydroxyalkylamide compounds such as bis[N,N-di(β-hydroxyethyl)]adipamide. Among these post-crosslinking agents, preferred are polyglycidyl compounds such as (poly) ethylene glycol diglycidyl ether, (poly)glycerin diglycidyl ether, (poly)glycerol triglycidyl ether, trimethylolpropane triglycidyl ether, (poly)propylene glycol polyglycidyl ether, (poly)glycerol polyglycidyl ether. These post-crosslinking agents may be used alone or in combination of two or more.

The used amount of a post-crosslinking agent is preferably 0.00001 to 0.01 mol relative to 1 mol of the total amount of a water-soluble ethylenically unsaturated monomer used for polymerization, more preferably 0.00005 to 0.005 mol and further preferably 0.0001 to 0.002 mol.

As a method of adding a post-crosslinking agent, the post-crosslinking agent may be added as it is or as an aqueous solution. A post-crosslinking agent may also be added as a solution in which a hydrophilic organic solvent is used as a solvent, if desired. Hydrophilic organic solvents include, for example, lower alcohols such as methyl alcohol, ethyl alcohol, n-propyl alcohol, isopropyl alcohol; ketones such as acetone, methyl ethyl ketone; ethers such as diethyl ether, dioxane, tetrahydrofuran; amides such as N,N-dimethylformamide; sulfoxides such as dimethyl sulfoxide. These hydrophilic organic solvents may be used alone or in combination of two or more, or may be used as a mixed solvent with water.

A post-crosslinking agent may be added after the polymerization reaction of water-soluble ethylenically unsaturated monomer has been almost completed, and it is preferably added in the presence of water in the range of 1 to 400 parts by mass relative to 100 parts by mass of a water-soluble ethylenically unsaturated monomer, more preferably added in the presence of water in the range of 5 to 200 parts by mass, further preferably added in the presence of water in the range of 10 to 100 parts by mass and further more preferably added in the presence of water in the range of 20 to 60 parts by mass. Note that the amount of water means the total amount of a water content in a reaction system and a water content used if desired when adding a post-crosslinking agent.

The reaction temperature in the post-crosslinking reaction, but it is preferably 50 to 250° C., more preferably 60 to 180° C., further preferably 60 to 140° C. and further more preferably 70 to 120° C. Further, the reaction time for the post-crosslinking reaction is preferably for 1 to 300 minutes, and more preferably for 5 to 200 minutes.

<Drying Step>

The method may comprise a drying step of removing water, a hydrocarbon dispersion medium and the like using distillation by applying energy such as heat from the outside after performing the aforementioned reversed phase suspension polymerization. When performing dehydration of a hydrous gel after reversed phase suspension polymerization, a system in which the hydrous gel is dispersed in a hydrocarbon dispersion medium is heated to temporarily evaporate water and the hydrocarbon dispersion medium from the system by azeotropic distillation. At this time, only the hydrocarbon dispersion medium evaporated is allowed to return into the system, enabling continuous azeotropic distillation. In that case, the temperature in the system during the drying treatment is maintained at or below the azeotropic temperature with the hydrocarbon dispersion medium. Therefore this is preferred in view of that, for example, the resin is less susceptible to deterioration. Water and the hydrocarbon dispersion medium is continuously evaporated away to obtain particles of a water-absorbent resin. By controlling processing conditions of this drying step after polymerization to adjust the amount of dehydrated water, various properties of the resulting water-absorbent resin can be controlled.

In the drying step, the drying treatment may be performed by distillation under ordinary pressure or under a reduced pressure. Further, the drying treatment may be performed under a gas flow of nitrogen and the like in view of increasing drying efficiency. When performing the drying treatment under ordinary pressure, a drying temperature is preferably 70 to 250° C., more preferably 80 to 180° C., further preferably 80 to 140° C. and further more preferably 90 to 130° C. Further, when performing the drying treatment under reduced pressure, a drying temperature is preferably 40 to 160° C., more preferably 50 to 110° C.

Note that in a case where post-crosslinking step is performed with a post-crosslinking agent after monomers are polymerized by reversed phase suspension polymerization, the drying step is performed by distillation as described above after the post-crosslinking step. Alternatively, the post-crosslinking step and the drying step may be performed simultaneously.

Further, if desired, various additives such as chelating agents, reducing agents, oxidizing agents, antibacterial agents, deodorizing agents may be added to a water-absorbent resin after polymerization, during or after drying.

3. Absorbent Material and Absorbent Article

The water-absorbent resin according to the present invention may constitute an absorbent material for use in, for example, hygienic materials such as sanitary goods and disposable diapers, and may suitably be used in absorbent articles comprising the above absorbent materials.

Here, an absorbent material in which a water-absorbent resin is used comprises, for example, the water-absorbent resin and a hydrophilic fiber. The structures of the absorbent material include a dispersion mixture obtained by mixing a water-absorbent resin and a hydrophilic fiber to give a uniform composition, a sandwich structure in which a water-absorbent resin is sandwiched between layered hydrophilic fibers, a structure in which a water-absorbent resin and a hydrophilic fiber is wrapped in tissue, and the like. Note that other components, for example, adhesive binder such as thermal adhesive synthetic fibers, hot melt adhesives, adhesive emulsions for increasing the shape retention capability of an absorbent material may be included in the absorbent material.

The content of a water-absorbent resin in an absorbent material is preferably 5 to 95 mass %, more preferably 20 to 90 mass % and further preferably 30 to 80 mass %.

Hydrophilic fibers include cellulose fibers prepared from wood such as cotton-like pulp, mechanical pulp, chemical pulp, semi-chemical pulp; artificial cellulose fibers such as rayon, acetate; fibers comprising synthetic resin such as hydrophilized polyamide, polyester and polyolefine.

Moreover, an absorbent material in which a water-absorbent resin is used can be held between a liquid permeable sheet (a top sheet) through which a liquid can pass and a liquid impermeable sheet (a back sheet) through which a liquid cannot pass to give an absorbent article. The liquid permeable sheet is arranged on the side to be in contact with the body while the liquid impermeable sheet is arranged opposite to the side to be in contact with the body.

Liquid permeable sheets include nonwoven of an air through type, a span bond type, a chemical bond type, a needle punch type and the like comprising fiber such as polyethylene, polypropylene, polyester, etc. and porous synthetic resin sheets and the like. Further, liquid impermeable sheets include synthetic resin films comprising a resin such as polyethylene, polypropylene, polyvinyl chloride and the like.

EXAMPLES

4. Example

Below, the present invention will be described in detail with reference to Examples and Comparative Examples. However, the present invention shall not in any way be limited to the following Examples and the like.

4-1. Method for Evaluation Test

[Evaluation Test of Water-Absorbent Resin]

Water-absorbent resins obtained from Examples 1 to 4, and Comparative Examples 1 to 6 below were subjected to various tests described below for evaluation. In the followings, each evaluation test method will be described.

(1) Water-Absorption Capacity of Physiological Saline Under a Load of 4.14 kPa

A water-absorption capacity of physiological saline under a load of 4.14 kPa of a water-absorbent resin was measured using a measurement apparatus X. A schematic arrangement structure of the measurement apparatus X is shown in FIG. 1.

The measurement apparatus X shown in FIG. 1 comprises a buret part 1, a conduit 2, a measurement stage 3, a measurement part 4 placed on the measurement stage 3. In the buret part 1, a rubber stopper 14 is connected to the upper part of a buret 10, and an air introducing pipe 11 and a cock 12 is connected to the lower part of the buret 10. Further, a cock 13 is attached to the upper part of the air introducing pipe 11. A conduit 2 connects the buret part 1 and the measurement stage 3. The diameter of the conduit 2 is 6 mm. The measurement stage 3 has a hole with a diameter of 2 mm at the center, to which the conduit 2 is connected. The measurement part 4 is provided with a cylinder 40 and a nylon mesh 41 patched on the bottom of the cylinder 40, as well as a weight 42. The inner diameter of the cylinder 40 is 2.0 cm. The nylon mesh 41 is formed as 200 mesh (75 μm openings). Further, it is configured such that a predetermined amount of a water-absorbent resin 5 is uniformly distributed on the nylon mesh 41. The weight 42 has a diameter of 1.9 cm and a mass of 119.6 g. The weight 42 is to be placed on the water-absorbent resin 5 to uniformly apply a load of 4.14 kPa to the water-absorbent resin 5.

Using the measurement apparatus X having a structure as described above, first, the cock 12 and the cock 13 at the buret part 1 were closed, and then physiological saline adjusted to 25° C. was introduced into the buret 10 from the top. Subsequently, the top of the buret was plugged with the rubber stopper 14, and then the cock 12 and the cock 13 at the buret part 1 were opened. Next, the height of the measurement stage 3 was adjusted so that the tip of the conduit 2 at the center of the measurement stage 3 is leveled with the air inlet of the air introducing pipe 11.

Meanwhile, 0.10 g of the water-absorbent resin 5 was uniformly distributed on the nylon mesh 41 in the cylinder 40, and then the weight 42 was placed on that water-absorbent resin 5. The measurement part 4 was arranged so that its center coincided with the conduit inlet at the center of the measurement stage 3.

The amount of reduced physiological saline in the buret 10 (the amount of physiological saline absorbed by the water-absorbent resin 5) Wa (mL) was continuously measured from the time point when the water-absorbent resin 5 started to absorb water. The water-absorption capacity of physiological saline under a load of 4.14 kPa at 60 minutes from the start of water absorption was calculated by the following formula.

Water-absorption capacity of physiological saline
under a load of 4.14 kPa (mL/g)=$Wa$/0.10 (g)

(2) Water-Absorption Rate of Physiological Saline

The water-absorption rate of physiological saline was measured in the room at a temperature adjusted to 25° C.±1° C. Physiological saline in an amount of 50.0±0.1 g adjusted to a temperature of 25±0.2° C. previously in a constant temperature water bath was stirred at 600 rpm with a magnetic stirrer bar (8 mm ø×30 mm without a ring) to generate a vortex. A test water-absorbent resin in an amount of 2.0±0.002 g was added in one portion to the above physiological saline, and a time (in seconds) until the vortex disappeared and the liquid surface became flat after addition of the water-absorbent resin was measured. The above time was taken as the water-absorption rate.

(3) Median Particle Diameter (Particle Size Distribution)

JIS standard sieves were combined in the following order from the top: a sieve of 850 μm openings, a sieve of 600 micrometers openings, a sieve of 500 μm openings, a sieve of 400 μm openings, a sieve of 300 μm openings, a sieve of 250 μm openings, a sieve 150 μm openings and a receiving tray.

A water-absorbent resin in an amount of 50 g was introduced on the top of the combined sieves, and then shaken for 20 minutes using a ro-tap shaker for classification. After classification, the mass of the water-absorbent resin which remained in each sieve was calculated as a mass proportion of particles relative to the total mass to obtain a particle size distribution. By integrating the amount on each sieve from the one having the largest particle diameter in this particle size distribution, the relationship between the sieve openings and the integrated value of the mass proportion of particles from the water-absorbent resin which remained in the sieves was plotted on logarithmic probability paper. By connecting the plots on the probability paper with a straight line, a particle diameter corresponding to 50 mass % in the integrated mass proportion of particles is taken as the median particle diameter.

Note that the mass proportion of particles from 300 to 400 μm in the total water-absorbent resin is a mass proportion of particles from a water-absorbent resin which remained in the sieve with 300 μm openings relative to the whole proportion in the aforementioned measurements. Similarly, the mass proportion of particles from 150 to 850 μm in the total water-absorbent resin is a value obtained by summing the mass proportion of particles of the water-absorbent resin which remained in sieves with openings of 150 μm, 250 μm, 300 μm, 400 μm, 500 μm, 600 μm.

(4) Preparation of Artificial-Urine

The following inorganic salts were dissolved in ion exchange water according to the composition shown below. To this, a small amount of Blue No. 1 was further blended to prepare artificial-urine.

<Composition of Artificial-Urine>
NaCl: 0.780 mass %
$CaCl_2$: 0.022 mass %
$MgSO_4$: 0.038 mass %

(5) Artificial-Urine Absorption Ratio

A cotton bag (cotton broadcloth No. 60, horizontal 100 mm× vertical 200 mm) into which 2.0 g of a water-absorbent resin was weighed out was placed into a 500 mL beaker. To the cotton bag containing the water-absorbent resin, 500 g of the aforementioned artificial-urine was poured in one portion, and the inside was lightly stirred so that lumps were not formed. The upper part of the cotton bag was then closed with a rubber band, and allowed to stand for 30 minutes to let the water-absorbent resin to swell freely. After 30 minutes passed, the above cotton bag containing the water-absorbent resin was dehydrated for 1 minute to remove excess water using a dehydrator (made by KOKUSAN Co., Ltd., Product number: H-122) configured to produce a centrifugal force of 167 G. Then the mass Wb (g) of the cotton bag containing the swollen gel after dehydration was measured. After the measurement, the swollen gel therein was removed, and then similar operations were performed using the empty cotton bag alone as a tare to determine the wet empty mass Wc (g), and then the artificial-urine absorption ratio was calculated according to the following formula to the first place of the decimal point.

Artificial-urine absorption ratio (g/g)=[$Wb-Wc$] (g)/
mass of water-absorbent resin (g)

(6) Amount of Liquid Flow

Figure 2:
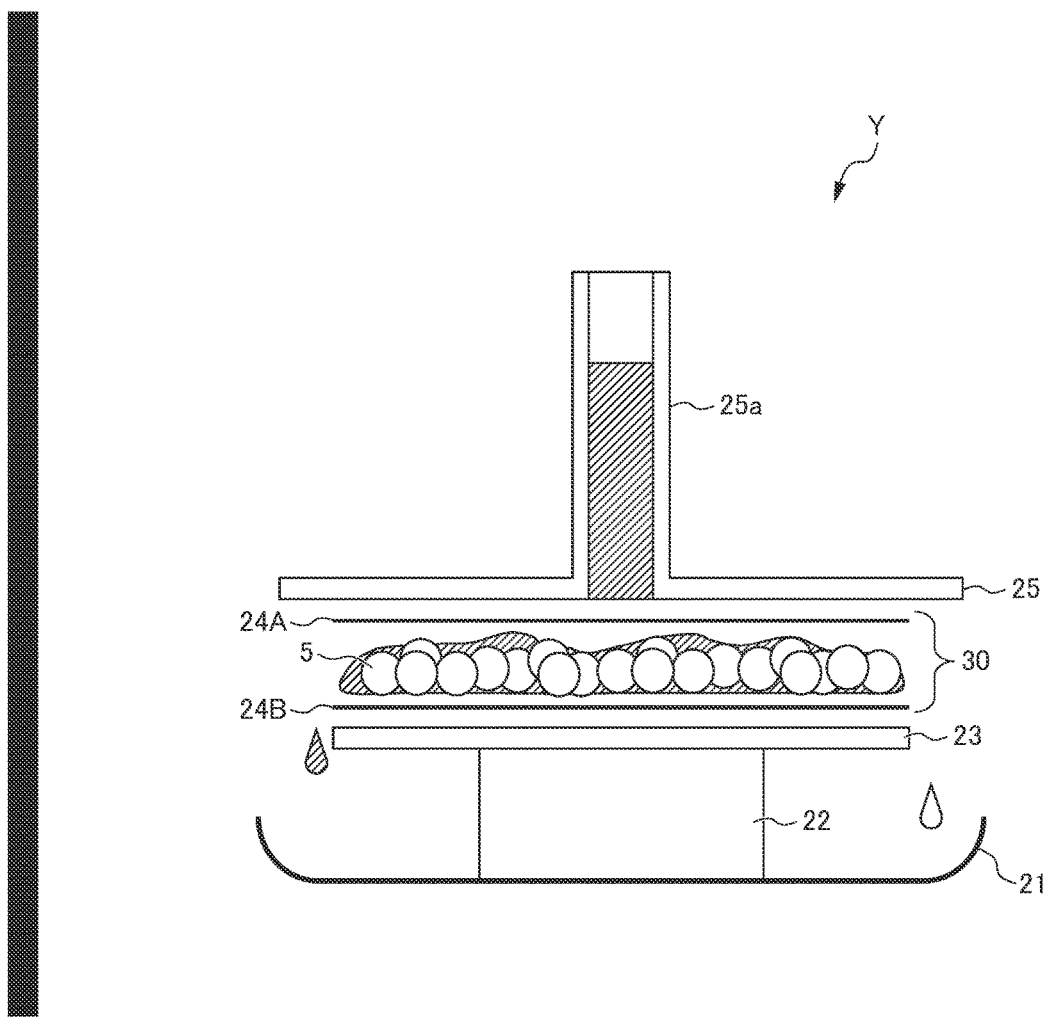
FIG. 2 shows a pattern diagram illustrating the structure of an apparatus for measuring, in a water-absorbent resin, the amount of liquid flow.

Liquid flow tests were performed using an apparatus Y shown in FIG. 2. The apparatus Y comprises a tray 21 for recovering a liquid for "the amount of liquid flow", a support stage 22, an acrylic plate 23 for holding a sample, a measurement sample 30 comprising a water-absorbent resin 5 sandwiched between nonwovens 24A and 24B from the above and below and an acrylic plate 25 having a cylinder-like inlet attached at the center.

First, the support stage 22, produced by SUS, with a height of 10 cm was placed on the metal tray 21 with 30×23 cm and a depth of 5 cm. On this, placed was the acrylic plate 23 with 16 cm×12 cm (thickness: 5 mm). The level of the upper portion of the acrylic plate 23 was confirmed with a level gauge. On this, placed was the nonwoven 24B (a polyethylene-polypropylene air-through porous liquid permeable sheet with a basis weight of 22 g/m$^2$) having the same size as the acrylic plate 23. The measurement sample 30 was prepared as follows: a 2 cm blank part from four edges was prepared in the nonwoven 24B, and 4.8 g of the water-absorbent resin 5 was uniformly dispersed over the portion inside the blank part (12 cm×8 cm), and then the nonwoven 24A of the same size was placed from the above so as to form a sandwiched configuration. On this, the acrylic plate 25 with a dimension of 48 cm×28 cm (mass: 840 g) having the cylinder-like inlet part 25*a* with an inner diameter of 3 cm and a height of 16.5 cm at the center was placed such that the central part of the cylinder coincided with the central part of the measurement sample 30.

Artificial-urine adjusted to a solution temperature of 25° C. in an amount of 120 g was introduced in one portion through the cylinder-like inlet part 25a. Next, the flow of artificial-urine was confirmed to have been stopped after the completion of permeation. Then the amount of artificial-urine flowed out of the acrylic plate 23 into the tray 21 was measured to obtain the mass thereof to the first place of the decimal point. This was taken as the amount of liquid flow (g).

[Evaluation Test of Absorbent Material and Absorbent Article in which Water-Absorbent Resin is Used]

(1) Production of Absorbent Material and Absorbent Article

Using 12 g of a water-absorbent resin and 12 g of crushed pulp (made by Rayonier, Rayfloc) were uniformly mixed by air papermaking to produce a sheet-like absorbent material core with a size of 40 cm×12 cm. Next, while the absorbent material core was placed between two tissue papers, which had the same size as the absorbent material core and a basis weight of 16 g/m2, the absorbent material core was all over pressed with a load of 196 kPa for 30 seconds to prepare an absorber absorbent material. Further, the absorbent article was prepared by arranging a polyethylene-polypropylene air-through porous liquid permeable sheet on the upper surface of the absorbent material, the sheet having a basis weight of 22 g/m$^2$ and the same size as the absorbent material, and arranging a polyethylene impermeable sheet of the same size and the same basis weight on the lower surface of the absorbent material.

(2) Permeation Time of Absorbent Article

The absorbent article was placed on a leveled table. A measurement device comprising a cylinder for introducing a liquid having an inner diameter of 3 cm was placed on the center of the absorbent article, and 80 mL of artificial-urine was introduced into the cylinder in one portion. Simultaneously with it, a time until the artificial-urine completely disappeared in the cylinder was measured using a stopwatch, which was taken as a first permeation time (in seconds). Then, the cylinder was removed, and the absorbent article was stored as it was. At 30 minutes and 60 minutes after the start of the first introduction of artificial-urine, second and third permeation times (in seconds) were also measured by placing the measurement device on the same position as in the first time and performing similar procedures. The total time of the first to third measurements were taken as the total permeation time. Note that the shorter is the permeation time, the better is the absorbent article.

(3) Amount of Re-Wet

At 120 minutes after the start of the first introduction of artificial-urine at the aforementioned measurement of permeation time, a filter paper of 10 cm square with a previously measured mass (Wd (g), about 50 g) was placed on the absorbent article near the introduction site of artificial-urine, on which a 5-Kg weight having a bottom surface of 10 cm×10 cm was placed. After applying the weight for 5 minutes, the mass of the filter paper (We (g)) was measured, and an increased amount in the mass was taken as the amount of re-wet (g). Note that the smaller is the amount of re-wet, the better is the absorbent article.

Amount of re-wet (g)=$We-Wd$ (4) Diffusion Length

Within 5 minutes after the aforementioned measurements of the amount of re-wet, a diffusion dimension (cm) in the longitudinal direction of the absorbent article into which the artificial-urine had been permeated was measured. Note values below the decimal point were rounded off.

4-2. Examples and Comparative Example

Example 1

A 2 L cylindrical round-bottom separable flask with an inner diameter of 110 mm was prepared which was equipped with a reflux condenser, a dropping funnel, a nitrogen gas-introducing tube and stirrer having stirring blades compound of two sets of 4 inclined paddle blades with a blade diameter of 50 mm. To this flask, 300 g of n-heptane as a hydrocarbon dispersion medium was introduced, and 0.74 g of HLB3 sucrose stearic acid ester (made by Mitsubishi-Kagaku Foods Corporation, Ryoto sugar ester S-370) as a surfactant and 0.74 g of maleic anhydride modified ethylene-propylene copolymer (made by Mitsui Chemicals, Inc., High Wax 1105A) as a polymeric dispersion agent were added, and heated to 80° C. with stirring to dissolve the surfactant, and then cooled to 50° C.

Meanwhile, 92 g (1.02 mol) of 80 mass % aqueous solution of acrylic acid was introduced into a 500 mL Erlenmeyer flask, and 146.0 g of 21 mass % aqueous solution of sodium hydroxide was added dropwise while cooling from the outside to perform 75 mol % neutralization. Subsequently, 0.092 g of hydroxylethyl cellulose (made by Sumitomo Seika Chemicals Co., Ltd., HEC AW-15F) as a thickener, 0.092 g (0.339 mmol) of 2,2'-azobis(2-amidinopropane)dihydrochloride as an azo based compound, 0.037 g (0.136 mmol) of potassium persulfate as a peroxide and 0.0101 g (0.058 mmol) of ethylene glycol diglycidyl ether as an internal-crosslinking agent were added and dissolved to prepare an aqueous monomer solution.

Then, the aqueous monomer solution prepared as described above was added to a separable flask with a stirrer at a rotation rate of 500 rpm, and the atmosphere in the system was thoroughly replaced with nitrogen. Then, the flask was immersed into a 70° C. water bath to raise temperature, and a first-step polymerization was performed for 60 minutes to obtain a first-step polymerized slurry.

Meanwhile, 128.8 g (1.43 mol) of 80 mass % aqueous solution of acrylic acid was introduced to another 500 mL Erlenmeyer flask, and 159.0 g of 27 mass % aqueous solution of sodium hydroxide was added dropwise while cooling from the outside to perform 75 mol % neutralization. Subsequently, 0.129 g (0.475 mmol) of 2,2'-azobis(2-amidinopropane)dihydrochloride as an azo based compound, 0.052 g (0.191 mmol) of potassium persulfate as a peroxide and 0.0116 g (0.067 mmol) of ethylene glycol diglycidyl ether as an internal-crosslinking agent were added and dissolved to prepare a second-step aqueous monomer solution.

After changing the stirring rotation rate to 1000 rpm after the above polymerization, and after cooling the system in the aforementioned separable flask to 25° C., all of the second-step aqueous monomer solution was added to the first-step polymerized slurry, and the atmosphere in the system was thoroughly replaced with nitrogen. Then the flask was again immersed into a 70° C. water bath to raise temperature, and a second-step polymerization was performed for 30 minutes.

After the second-step polymerization, the reaction liquid was heated to 125° C. in an oil bath, and 239 g of water was removed from the system by refluxing n-heptane in azeotropic distillation of n-heptane and water. Then, 4.42 g (0.51 mmol) of 2 mass % solution of aqueous ethylene glycol diglycidyl ether was added as a post-crosslinking agent, and maintained at 80° C. for 2 hours. Subsequently, drying was performed by evaporating n-heptane, and then a dried resin was obtained. This dried resin was mixed with 0.3 mass % of amorphous silica (made by Evonik Degussa Japan, Inc., Carplex #80), and allowed to pass through a sieve with 1000 μm openings to obtain 234.0 g of a water-absorbent resin in a form of agglomerated spherical particles. This water-absorbent resin was evaluated in accordance with the various test methods as described above.

Note that in the resulting water-absorbent resin, the mass proportion of particles from 150 to 850 μm relative to the whole proportion was 95.5 mass %, and the mass proportion of particles from 300 to 400 μm relative to the whole proportion was 25.0 mass %. Further, the water-absorption rate of physiological saline of the resulting water-absorbent resin was 60 seconds.

Example 2

In Example 2, the same procedures were performed as in Example 1 except that 242 g of water was removed from the system by refluxing n-heptane in azeotropic distillation of n-heptane and water after the second-step polymerization to obtain 231.8 g of a water-absorbent resin in a form of secondary particles in which spherical primary particles were agglomerated. Thereby, a water-absorbent resin was obtained having a different water-retention capacity from the water-absorbent resin obtained in Example 1. This water-absorbent resin was evaluated in accordance with the various test methods as described above.

Note that in the resulting water-absorbent resin, the mass proportion of particles from 150 to 850 μm relative to the whole proportion was 96.6 mass %, and the mass proportion of particles from 300 to 400 μm relative to the whole proportion was 27.6 mass %. Further, the water-absorption rate of physiological saline of the resulting water-absorbent resin was 66 seconds.

Example 3

In Example 3, the same procedures were performed as in Example 1 except that 236 g of water was removed from the system by refluxing n-heptane in azeotropic distillation of n-heptane and water after the second-step polymerization to obtain 230.7 g of a water-absorbent resin in a form of secondary particles in which spherical primary particles were agglomerated. Thereby, a water-absorbent resin was obtained having a different water-retention capacity from the water-absorbent resin obtained in Example 1. This water-absorbent resin was evaluated in accordance with the various test methods as described above.

Note that in the resulting water-absorbent resin, the mass proportion of particles from 150 to 850 μm relative to the whole proportion was 96.3 mass %, and the mass proportion of particles from 300 to 400 μm relative to the whole proportion was 25.3 mass %. Further, the water-absorption rate of physiological saline of the resulting water-absorbent resin was 78 seconds.

Example 4

In Example 4, the same procedures were performed as in Example 1 except that the stirring rotation rate at the first-step polymerization was changed to 550 rpm, and the amount of 2 mass % aqueous solution of ethylene glycol diglycidyl ether as a post-crosslinking agent was changed to 6.62 g to obtain 231.4 g of a water-absorbent resin in a form of secondary particles in which spherical primary particles were agglomerated. This water-absorbent resin was evaluated in accordance with the various test methods as described above.

Note that in the resulting water-absorbent resin, the mass proportion of particles from 150 to 850 μm relative to the whole proportion was 97.4 mass %, and the mass proportion of particles from 300 to 400 μm was 42.1 mass %. Further, the water-absorption rate of physiological saline of the resulting water-absorbent resin was 63 seconds.

Comparative Example 1

In Comparative Example 1, only a peroxide was used alone to perform reversed phase suspension polymerization for production of a water-absorbent resin.

A 2 L cylindrical round-bottom separable flask with an inner diameter of 110 mm was prepared which was equipped with a reflux condenser, a dropping funnel, a nitrogen gas-introducing tube and stirrer having stirring blades compound of two sets of 4 inclined paddle blades with a blade diameter of 50 mm. To this flask, 300 g of n-heptane as a hydrocarbon dispersion medium was introduced, and 0.74 g of HLB3 sucrose stearic acid ester (made by Mitsubishi-Kagaku Foods Corporation, Ryoto sugar ester S-370) as a surfactant and 0.74 g of maleic anhydride modified ethylene-propylene copolymer (made by Mitsui Chemicals, Inc., High Wax 1105A) as a polymeric dispersion agent were added, and heated to 80° C. with stirring to dissolve the surfactant, and then cooled to 50° C.

Meanwhile, 92 g (1.02 mol) of 80 mass % aqueous solution of acrylic acid was introduced into a 500 mL Erlenmeyer flask, and 146.0 g of 21 mass % aqueous solution of sodium hydroxide was added dropwise while cooling from the outside to perform 75 mol % neutralization. Subsequently, 0.092 g of hydroxylethyl cellulose (made by Sumitomo Seika Chemicals Co., Ltd., HEC AW-15F) as a thickener, 0.074 g (0.274 mmol) of potassium persulfate and 0.0184 g (0.1056 mmol) of ethylene glycol diglycidyl ether as an internal-crosslinking agent were added and dissolved to prepare an aqueous monomer solution.

Then, the aqueous monomer solution prepared as described above was added to a separable flask with a stirrer at a rotation rate of 500 rpm, and the atmosphere in the system was thoroughly replaced with nitrogen. Then, the flask was immersed into a 70° C. water bath to raise temperature, and a first-step polymerization was performed for 60 minutes to obtain a first-step polymerized slurry.

Meanwhile, 128.8 g (1.43 mol) of 80 mass % aqueous solution of acrylic acid was introduced to another 500 mL Erlenmeyer flask, and 159.0 g of 27 mass % aqueous solution of sodium hydroxide was added dropwise while cooling from the outside to perform 75 mol % neutralization. Subsequently, 0.104 g (0.382 mmol) of potassium persulfate and 0.0386 g (0.2218 mmol) of ethylene glycol diglycidyl ether as an internal-crosslinking agent were added and dissolved to prepare a second-step aqueous monomer solution.

The stirring rotation rate was changed to 1000 rpm after the polymerization, and the system in the aforementioned separable flask was cooled to 25° C., and then all of the second-step aqueous monomer solution was added to the first-step polymerized slurry, and the atmosphere in the system was thoroughly replaced with nitrogen. Then the flask was again immersed into a 70° C. water bath to raise temperature, and a second-step polymerization was performed for 30 minutes.

After the second-step polymerization, the reaction liquid was heated to 125° C. in an oil bath, and 273 g of water was withdrawn from the system by refluxing n-heptane in azeotropic distillation of n-heptane and water. Then, 6.62 g (0.76 mmol) of 2 mass % aqueous solution of ethylene glycol diglycidyl ether was added as a post-crosslinking agent, and maintained at 80° C. for 2 hours. Subsequently, drying was performed by evaporating n-heptane to obtain a dried resin. This dried resin was mixed with 0.3 mass % of amorphous silica (made by Evonik Degussa Japan, Inc., Carplex #80), and allowed to pass through a sieve with 1000 μm openings to obtain 231.2 g of a water-absorbent resin in a form of agglomerated spherical particles. This water-absorbent resin was evaluated in accordance with the various test methods as described above.

Note that for the water-absorbent resin obtained, the mass proportion of particles from 150 to 850 μm relative to the whole proportion was 97.0 mass %, and the mass proportion of particles from 300 to 400 μm relative to the whole proportion was 36.9 mass %. Further, the water-absorption rate of physiological saline of the resulting water-absorbent resin was 41 seconds.

Comparative Example 2

In Comparative Example 2, the same procedures were performed as in Comparative Example 1 except that the amount of ethylene glycol diglycidyl ether added to the second-step monomer was changed to 0.0129 g, and the amount of 2 mass % aqueous solution of ethylene glycol diglycidyl ether as a post-crosslinking agent was changed to 4.42 g to obtain 232.9 g of a water-absorbent resin in a form of secondary particles in which spherical primary particles were agglomerated. This water-absorbent resin was evaluated in accordance with the various test methods as described above.

Note that for the water-absorbent resin obtained, the mass proportion of particles from 150 to 850 μm relative to the whole proportion was 96.4 mass %, and the mass proportion of particles from 300 to 400 μm relative to the whole proportion was 35.7 mass %. Further, the water-absorption rate of physiological saline of the resulting water-absorbent resin was 39 seconds.

Comparative Example 3

In Comparative Example 3, the same procedures were performed as in Comparative Example 1 except that the amount of ethylene glycol diglycidyl ether added to the first-step monomer was changed to 0.0101 g, and the stirring rotation rate at the first-step polymerization was changed to 550 rpm to perform the first-step polymerization, and then the amount of ethylene glycol diglycidyl ether added to the second-step monomer was changed to 0.0116 g, and the amount of 2 mass % aqueous solution of ethylene glycol diglycidyl ether as a post-crosslinking agent was changed to 4.42 g to obtain 231.8 g of a water-absorbent resin in a form of secondary particles in which spherical primary particles were agglomerated. This water-absorbent resin was evaluated in accordance with the various test methods as described above.

Note that in the resulting water-absorbent resin, the mass proportion of particles from 150 to 850 μm relative to the whole proportion was 94.6 mass %, and the mass proportion of particles from 300 to 400 μm relative to the whole proportion was 34.0 mass %. Further, the water-absorption rate of physiological saline of the resulting water-absorbent resin was 35 seconds.

Comparative Example 4

In Comparative Example 4, the same procedures were performed as in Comparative Example 1 except that the amount of ethylene glycol diglycidyl ether added to the first-step monomer was changed to 0.0156 g, the amount of ethylene glycol diglycidyl ether added to the second-step monomer was changed to 0.0155 g, and the amount of 2 mass % aqueous solution of ethylene glycol diglycidyl ether as a post-crosslinking agent was changed to 6.62 g to obtain 231.4 g of a water-absorbent resin in a form of secondary particles in which spherical primary particles were agglomerated. This water-absorbent resin was evaluated in accordance with the various test methods as described above.

Note that in the resulting water-absorbent resin, the mass proportion of particles from 150 to 850 μm relative to the whole proportion was 97.1 mass %, and the mass proportion of particles from 300 to 400 μm relative to the whole proportion was 35.9 mass %. Further, the water-absorption rate of physiological saline of the resulting water-absorbent resin was 40 seconds.

Comparative Example 5

In Comparative Example 5, the same procedures were performed as in Comparative Example 4 except that the temperature inside the separable flask before introducing the second-step aqueous monomer solution was changed to 23° C. to obtain 230.8 g of a water-absorbent resin in a form of secondary particles in which spherical primary particles were agglomerated. Thereby, a water-absorbent resin was obtained having a different median particle diameter from the water-absorbent resin obtained in Comparative Example 4. This water-absorbent resin was evaluated in accordance with the various test methods as described above.

Note that in the resulting water-absorbent resin, the mass proportion of particles from 150 to 850 μm relative to the whole proportion was 96.4 mass %, and the mass proportion of particles from 300 to 400 μm relative to the whole proportion was 23.2 mass %. Further, the water-absorption rate of physiological saline of the resulting water-absorbent resin was 51 seconds.

Comparative Example 6

In Comparative Example 6, the same procedures were performed as in Comparative Example 1 except that the amount of ethylene glycol diglycidyl ether added to the first-step monomer was changed to 0.0092 g, the amount of ethylene glycol diglycidyl ether added to the second-step monomer was changed to 0.0386 g, and the amount of 2 mass % aqueous solution of ethylene glycol diglycidyl ether as a post-crosslinking agent was changed to 11.04 g to obtain 231.0 g of a water-absorbent resin in a form of secondary particles in which spherical primary particles were agglomerated. This water-absorbent resin was evaluated in accordance with the various test methods as described above.

Note that in the resulting water-absorbent resin, the mass proportion of particles from 150 to 850 μm relative to the whole proportion was 92.9 mass %, and the mass proportion of particles from 300 to 400 μm relative to the whole proportion was 36.6 mass %. Further, the water-absorption rate of physiological saline of the resulting water-absorbent resin was 48 seconds.

4-3. Evaluation Results

[Evaluation Results of Water-Absorbent Resin]

Evaluation results of the water-absorbent resins are shown below in Table 1. Note that Table 1 also shows the absorbent material effective indices K defined by the following formula (I):

Absorbent material effective index $K$=the amount of liquid flow (g)×the artificial-urine absorption ratio (g/g)   (I)

TABLE 1

| | Water-absorption capacity under a load of 4.14 kPa (ml/g) | Meidan particle diameter (μm) | Artificial-urine absorption ratio (g/g) | Amount of liquid flow (g) | Absorbent material effective index K |
|---|---|---|---|---|---|
| Example 1 | 27 | 440 | 39.4 | 12.9 | 508 |
| Example 2 | 23 | 430 | 43.7 | 8.0 | 347 |
| Example 3 | 26 | 430 | 36.3 | 26.0 | 944 |
| Example 4 | 24 | 360 | 39.8 | 12.1 | 481 |
| Comparative Example 1 | 26 | 360 | 29.4 | 4.1 | 121 |
| Comparative Example 2 | 25 | 350 | 33.3 | 2.2 | 73 |
| Comparative Example 3 | 15 | 360 | 37.8 | 0.0 | 0 |
| Comparative Example 4 | 21 | 335 | 39.1 | 0.0 | 0 |
| Comparative Example 5 | 18 | 450 | 39.9 | 0.0 | 0 |
| Comparative Example 6 | 26 | 360 | 25.4 | 7.1 | 180 |

[Evaluation Results of Absorbent Articles]

Next, shown in Table 2 below are measurement results of the permeation time, the amount of re-wet, the diffusion length of artificial-urine for absorbent articles produced using the water-absorbent resins obtained from Examples 1, 2 and 3 and Comparative Examples 1, 2 and 3 as described above.

TABLE 2

| | Permeation time (s) | | | | Amount of Re-wet (g) | Diffusion length (cm) |
|---|---|---|---|---|---|---|
| | 1 | 2 | 3 | Total | | |
| Example 1 | 23 | 24 | 27 | 74 | 4.5 | 25 |
| Example 2 | 25 | 27 | 32 | 84 | 6.1 | 22 |
| Example 3 | 23 | 24 | 32 | 79 | 4.1 | 25 |
| Comparative Example 1 | 22 | 26 | 29 | 77 | 34.8 | 23 |
| Comparative Example 2 | 23 | 29 | 35 | 87 | 30.2 | 22 |
| Comparative Example 3 | 24 | 33 | 53 | 110 | 29.8 | 21 |

EXPLANATION OF REFERENCE NUMERALS

X Measuring apparatus (the water-absorption capacity of physiological saline under a load of 4.14 kPa)
Y Measuring apparatus (Liquid flow tests)
1 Buret part
2 Conduit
3 Measurement stage
4 Measurement part
5 Water-absorbent resin

The invention claimed is:

1. A method for producing a water-absorbent resin, comprising the steps of:
    obtaining a polymer by polymerizing a water-soluble ethylenically unsaturated monomer in the presence of an internal-crosslinking agent and in the coexistence of an azo based compound and a peroxide, and
    performing post-crosslinking of the polymer with a post-crosslinking agent to obtain a water-absorbent resin, wherein
    the water-absorbent resin has an absorbent material effective index K of 250 or more as determined in a liquid flow test defined below using the water-absorbent resin, the absorbent material effective index K being defined by the formula (I):

Absorbent material effective index $K$=the amount of liquid flow (g)×the artificial-urine absorption ratio (g/g)   (I)

wherein the artificial-urine absorption ratio is 36.0 g/g or more and 60.0 g/g or less [Liquid flow test]
the liquid flow test being performed as follows: a nonwoven is placed on an acrylic plate, and 4.8 g of the water-absorbent resin is uniformly dispersed thereon, and then another nonwoven is placed thereover so as to form a sandwiched configuration to give a measurement sample; next, acrylic plate having a cylinder-like inlet part with an inner diameter of 3 cm at a center is placed thereover so that the center of the cylinder coincides with the center of the measurement sample, and then 120 g of artificial-urine at a liquid temperature of 25° C. is introduced in one portion through the cylinder-like inlet part, and the amount of artificial-urine flowed out of the acrylic plate is measured, thereby obtaining the amount of liquid flow (g).

2. The method for producing a water-absorbent resin according to claim 1, wherein the amount of liquid flow is 5.0 g or more.

3. The method of claim 1, further comprising forming an absorbent article comprising the water-absorbent resin.

4. The method of claim 2, further comprising forming an absorbent article comprising the water-absorbent resin.

5. The method for producing a water-absorbent resin according to claim 1, wherein the used proportion of the azo based compound is 40 mass % or more relative to the total used amount of the azo based compound and the peroxide.

6. The method for producing a water-absorbent resin according to claim 1, wherein the used amount of the internal-crosslinking agent is 0.000001 to 0.002 mol relative to 1 mol of the water-soluble ethylenically unsaturated monomer.

* * * * *